United States Patent [19]

Baker et al.

[11] Patent Number: 5,705,710
[45] Date of Patent: Jan. 6, 1998

[54] PROCESS FOR THE SYNTHESIS OF HEXAFLUOROISOPROPYL ETHERS

[75] Inventors: Max T. Baker; John H. Tinker, both of Iowa City, Iowa; Jan A. Ruzicka, Dahlonega, Ga.

[73] Assignee: University of Iowa Research Foundation, Iowa City, Iowa

[21] Appl. No.: 783,758

[22] Filed: Jan. 15, 1997

[51] Int. Cl.⁶ .................................................. C07C 41/00
[52] U.S. Cl. .................................................. 568/683; 568/682
[58] Field of Search ................................... 568/683, 682

[56] References Cited

U.S. PATENT DOCUMENTS 3,346,448  10/1967  Gilbert.
4,250,334  2/1981  Coon.

*Primary Examiner*—Samuel Barts
*Attorney, Agent, or Firm*—Charles F. Lind

[57] ABSTRACT

This invention relates to a method of synthesizing 1,1,1,3,3,3-hexafluoroisopropyl ether compounds from the reaction of methoxymalanonitrile with a bromine trifluoride composition.

17 Claims, No Drawings

PROCESS FOR THE SYNTHESIS OF HEXAFLUOROISOPROPYL ETHERS

BACKGROUND OF THE INVENTION

Ethers that contain a $(CF_3)_2CH-O-$ group are 1,1,1,3,3,3-hexafluoroisopropyl ethers. The numbers 1 and 3 represent fluorines and the propyl carbons on which each is attached. 1,1,1,3,3,3-Hexafluoroisopropyl ethers include the desirable anesthetic sevoflurane (fluoromethyl 1,1,1,3,3,3-hexafluoroisopropyl ether) and compounds that are useful in making sevoflurane. The structure of sevoflurane is shown below in figure 1.

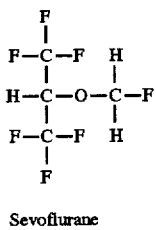

Sevoflurane 1,1,1,3,3,3-Hexafluoroisopropyl ethers are synthesized by various methods usually using expensive starting materials, such as hexafluoroisopropanol, and/or involving uneconomical multiple step processes.

Methyl 1,1,1,3,3,3-hexafluoroisopropyl ether, shown below in figure 2, may be synthesized by the reaction of hexafluoroisopropanol, a relatively expensive compound, with a methylating agent such as dimethyl sulfate or methyl iodide (U.S. Pat. No. 3,346,448).

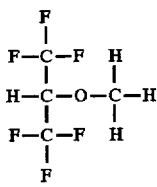

Methyl 1,1,1,3,3,3-Hexafluoroisopropyl Ether

Sevoflurane can be made by reacting hexafluoroisopropanol with formaldehyde and hydrogen fluoride (U.S. Pat. No. 3,683,092; U.S. Pat. No. 4,250,334).

Other methods used to make hexafluoroisopropyl ethers include the conversion of 1,1,1,3,3,3-hexachloroisopropyl ethers to 1,1,1,3,3,3-hexafluoroisopropyl ethers. For example, methyl 1,1,1,3,3,3-hexachloroisopropyl ether and chloromethyl 1,1,1,3,3,3-hexachloroisopropyl ether can be converted to sevoflurane by reaction of each of the above compounds with bromine trifluoride ($BrF_3$). They can also be made by reacting each of these chlorinated compounds with hydrogen fluoride, followed by reaction with $BrF_3$ (U.S. Pat. No. 4,874,902). The chlorine replacement methods are not desirable because large volumes of chlorine are released in the synthetic process, the yields are low, and multiple chloro-fluoro intermediates are formed. The intermediates must be removed to obtain the final ether product, sevoflurane. The purification processes increase the difficulty and cost of synthesis of 1,1,1,3,3,3-hexafluoroisopropyl ethers by this method. Therefore, simple economical methods for the synthesis of 1,1,1,3,3,3-hexafluoroisopropyl ethers are desirable.

SUMMARY OF THE INVENTION

This invention relates to, and an object of this invention is to provide a method of synthesizing 1,1,1,3,3,3-hexafluoroisopropyl ether compounds, including, or, such as sevoflurane (see figure 1), from methoxymalononitrile, a compound also known as α,α-dicyanomethyl methyl ether, and having the formula $(CN)_2CHOCH_3$, and having the chemical structure shown below in figure 3.

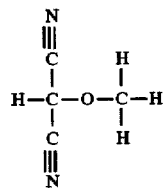

Methoxymalononitrile

Another object of this invention is to provide a method for synthesizing the compound methyl 1,1,1,3,3,3-hexafluoroisopropyl ether (see figure 2).

Yet another object of the invention is to provide a method for synthesizing the compound sevoflurane (see figure 1).

A more detailed object of the invention is to provide a method for synthesizing each or both of the above-identified 1,1,1,3,3,3-hexafluoroisopropyl ether compounds in a single step reaction involving the compound methoxymalononitrile (see figure 3) and a bromine trifluoride composition.

DETAILED DESCRIPTION OF THE INVENTION

The applicants discovered that the highly reactive oxidizing and fluorinating $BrF_3$ composition, unexpectedly reacts with methoxymalononitrile, $(CN)_2CHOCH_3$ (see figure 3), an ether compound that contains two cyano (—CN) groups on a carbon bound to an ether oxygen, to produce methyl 1,1,1,3,3,3-hexafluoroisopropyl ether and fluoromethyl 1,1,1,3,3,3-hexafluoroisopropyl ethers (sevoflurane). The reaction is performed without the need of a solvent and at easily obtained and maintained temperatures. $BrF_3$ is a composition that is made by combining elemental fluorine ($F_2$) with elemental bromine ($Br_2$), and it contains, in addition to $BrF_3$, the compounds BrF, $BrF_2$, $BrF_4$, and $Br_2$ (J. Org. Chem. 32:3478,1967). The $BrF_3$ composition reacts with methoxymalononitrile to form these hexafluoroisopropyl ethers in the absence of a solvent, at temperatures between about 20° C. and 60° C., and without destruction of the methoxymalononitrile molecule. The $BrF_3$ composition also reacts with methoxymalononitrile to form these products without the evolution of chlorine gas and without the formation of significant amounts of undesired intermediates and alternate products.

The detailed synthesis of methyl 1,1,1,3,3,3-hexafluoroisopropyl ether and sevoflurane is described below. Methoxymalononitrile, $(CN)_2CHOCH_3$ (see figure 3) (0.75 g), is placed in a 100 ml glass flask. The vessel is sealed other than an outlet connected to a dry-ice trap for collecting effluent vapors. The reaction vessel is placed in a water bath maintained approximately between 20° C. and 60° C. and the methoxymalononitrile is stirred with a magnetic stirrer. No solvent is added to the methoxymalononitrile. A bromine trifluoride composition, in liquid form with no solvent added, is slowly and continuously added for a one hour period via an inlet tube made of teflon into the reaction flask. A slow rate of addition of the $BrF_3$ composition is preferred to minimize the occurrence of a vigorous reaction. Products are evolved in the gas phase and condensed and collected as a liquid in the cold trap cooled to −78° C. by dry ice. Collection of the products is facilitated by increasing the reaction vessel temperature to approximately 60° C. or above. Completion of the reaction can be determined by the cessation of product formation due to depletion of methoxymalononitrile. Analysis of the collected product by flame ionization gas chromatography showed that it contained two major components in a quantity ratio of about 1 to 1.

The two product components as analyzed by gas chromatography/mass spectrometry were determined to be:

Methyl 1,1,1,3,3,3-Hexafluoroisopropyl ether, Component A in figure 4, a compound having the formula $(CF_3)_2CHOCH_3$, and previously defined in figure 2. and Fluoromethyl 1,1,1,3,3,3-hexafluoropropyl ether (sevoflurane), Component B in figure 4, a compound having the formula $(CF_3)_2CHOCH_2F$, and previously defined in figure 1.

The reaction of this invention is shown below:

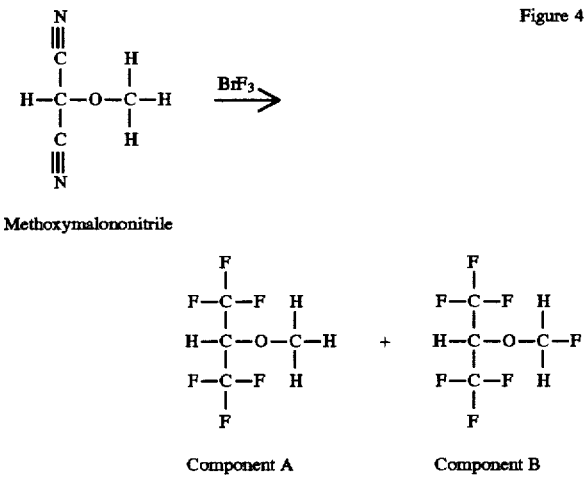

Component A of this reaction, methyl 1,1,1,3,3,3-hexafluoroisopropyl ether (see figure 2), can be purified from the reaction mixture by conventional means, or it can be returned to the reaction vessel containing the $BrF_3$ composition and converted to sevoflurane by monofluorination. Component B of this reaction, sevoflurane (see figure 1), can be purified by conventional means, such as by distillation, and used as an anesthetic.

The results of this invention are not predictable because more commonly, $BrF_3$ compositions, which are powerful oxidant compositions, will react with an organic molecule not to result in fluorine additions to that molecule, but the destruction of that molecule. It is not predictable that an organic compound having a carbon atom bound to two cyano groups and having the same carbon also bound to an oxygen in an ether linkage, will be converted to a 1,1,1,3,3,3-hexafluoroisopropyl ether structure when reacted with a $BrF_3$ composition. Nor is it predictable that an organic compound having a carbon atom bound to two cyano groups and having the same carbon also bound to an oxygen in an ether linkage, will react with a $BrF_3$ composition to form a 1,1,1,3,3,3-hexafluoroisopropyl ether structure in the absence of a solvent and at temperatures that range from approximately from 20° C. to 60° C.

What is claimed is:

1. A method of synthesizing methyl 1,1,1,3,3,3-hexafluoroisopropyl ether comprising the reaction of methoxymalononitrile with a bromine trifluoride composition.

2. A method of synthesizing methyl 1,1,1,3,3,3-hexafluoroisopropyl ether according to claim 1, comprising having the reaction of methoxymalononitrile with a bromine trifluoride composition at temperatures between approximately 20° C. and 60° C.

3. A method of synthesizing methyl 1,1,1,3,3,3-hexafluoroisopropyl ether according to claim 2, comprising having the reaction of a bromine trifluoride composition with methoxymalononitrile in the absence of a solvent.

4. A method of synthesizing methyl 1,1,1,3,3,3-hexafluoroisopropyl ether according to claim 3, comprising having the reaction of methoxymalononitrile with a bromine trifluoride composition comprised of BrF, $BrF_2$, $BrF_3$, $BrF_4$ and $Br_2$.

5. A method of synthesizing methyl 1,1,1,3,3,3-hexafluoroisopropyl ether according to claim 4, comprising having the reaction of a bromine trifluoride composition with methoxymalononitrile in a sealed vessel with the components liquified and agitated, and discharging gas products via a cold trap to condense and collect the said methyl 1,1,1,3,3,3-hexafluoroisopropyl ether.

6. A method of synthesizing fluoromethyl 1,1,1,3,3,3-hexafluoroisopropyl ether (sevoflurane) by reacting methoxymalononitrile with a bromine trifluoride composition.

7. A method of synthesizing fluoromethyl 1,1,1,3,3,3-hexafluoroisopropyl ether (sevoflurane) according to claim 6, comprising having the reaction of methoxymalononitrile with a bromine trifluoride composition at temperatures between approximately 20° C. and 60° C.

8. A method of synthesizing fluoromethyl 1,1,1,3,3,3-hexafluoroisopropyl ether (sevoflurane) according to claim 7, comprising having the reaction of a bromine trifluoride composition with methoxymalononitrile in the absence of a solvent.

9. A method of synthesizing fluoromethyl 1,1,1,3,3,3-hexafluoroisopropyl ether (sevoflurane) according to claim 8, comprising having the reaction of methoxymalononitrile with a bromine trifluoride composition comprised of BrF, $BrF_2$, $BrF_3$, $BrF_4$ and $Br_2$.

10. A method of synthesizing fluoromethyl 1,1,1,3,3,3-hexafluoroisopropyl ether (sevoflurane) according to claim 9, comprising having the reaction of methoxymalononitrile with a bromine trifluoride composition in a sealed vessel with the components liquified and agitated, and discharging gas products via a cold trap to condense and collect the said sevoflurane.

11. A method of synthesizing fluoromethyl 1,1,1,3,3,3-hexafluoroisopropyl ether (sevoflurane), comprising first synthesizing methyl 1,1,1,3,3,3-hexafluoroisopropyl ether according to claim 5, and then returning the synthesized methyl 1,1,1,3,3,3-hexafluoroisopropyl ether to the sealed vessel and bromine trifluoride composition for synthesizing fluoromethyl 1,1,1,3,3,3-hexafluoroisopropyl ether (sevoflurane) according to the continuation of the reaction of claim 5.

12. A method of simultaneously synthesizing fluoromethyl 1,1,1,3,3,3-hexafluoroisopropyl ether (sevoflurane) and methyl 1,1,1,3,3,3-hexafluoroisopropyl ether by reacting methoxymalononitrile with a bromine trifluoride composition.

13. A method of simultaneously synthesizing fluoromethyl 1,1,1,3,3,3-hexafluoroisopropyl ether (sevoflurane) and methyl 1,1,1,3,3,3-hexafluoroisopropyl ether according to claim 12, comprising having the reaction of methoxymalononitrile with a bromine trifluoride composition at temperatures between approximately 20° C. and 60° C.

14. A method of simulaneously synthesizing fluoromethyl 1,1,1,3,3,3-hexafluoroisopropyl ether (sevoflurane) and methyl 1,1,1,3,3,3-hexafluoroisopropyl ether according to claim 13, comprising having the reaction of a bromine trifluoride composition with methoxymalononitrile in the absence of a solvent.

15. A method of simultaneously synthesizing fluoromethyl 1,1,1,3,3,3-hexafluoroisopropyl ether (sevoflurane) and methyl 1,1,1,3,3,3-hexafluoroisopropyl ether according to claim 14, comprising having the reaction of of methoxymalononitrile with a bromine trifluoride composition comprised of BrF, $BrF_2$, $BrF_3$, $BrF_4$ and $Br_2$.

16. A method of simultaneously synthesizing methyl 1,1,1,3,3,3-hexafluoroisopropyl ether and fluoromethyl 1,1,1,3,3,3-hexafluoroisopropyl ether (sevoflurane) according to claim 15, comprising having the reaction of methoxymalononitrile with a bromine trifluoride composition in a sealed vessel with the components liquidified and agitated, and discharging gas products via a cold trap to condense and collect the said ethers.

17. A method of synthesizing fluoromethyl 1,1,1,3,3,3-hexafluoroisopropyl ether (sevoflurane), according to claim 16, comprising returning the synthesized methyl 1,1,1,3,3,3-hexafluoroisopropyl ether back to the sealed vessel and bromine trifluoride for synthesizing fluoromethyl 1,1,1,3,3,3-hexafluoroisopropyl ether (sevoflurane) according to the continuation of the reaction of claim 16.

* * * * *